(12) United States Patent
Makino

(10) Patent No.: US 8,523,846 B2
(45) Date of Patent: Sep. 3, 2013

(54) CORNEAL SURGERY APPARATUS

(75) Inventor: Hirokatsu Makino, Toyohashi (JP)

(73) Assignee: Nidek Co., Ltd., Gamagori-shi (JP)

( * ) Notice: Subject to any disclaimer, the term of this patent is extended or adjusted under 35 U.S.C. 154(b) by 1087 days.

(21) Appl. No.: 12/312,814

(22) PCT Filed: Nov. 29, 2007

(86) PCT No.: PCT/JP2007/073105
§ 371 (c)(1),
(2), (4) Date: May 28, 2009

(87) PCT Pub. No.: WO2008/066135
PCT Pub. Date: Jun. 5, 2008

(65) Prior Publication Data
US 2010/0057059 A1 Mar. 4, 2010

(30) Foreign Application Priority Data
Nov. 29, 2006 (JP) .................. 2006-322648

(51) Int. Cl.
*A61B 18/18* (2006.01)
(52) U.S. Cl.
USPC ........................................... 606/4
(58) Field of Classification Search
USPC ..................... 606/4, 5, 10, 11, 12
See application file for complete search history.

(56) References Cited

U.S. PATENT DOCUMENTS

| | | | |
|---|---|---|---|
| 5,187,506 A | 2/1993 | Carter | |
| 5,508,759 A | 4/1996 | Konishi et al. | |
| 5,640,610 A | 6/1997 | Sato et al. | |
| 6,159,202 A | 12/2000 | Sumiya et al. | |
| 6,655,805 B2 | 12/2003 | Fujieda | |
| 7,118,561 B2 | 10/2006 | Sugiura | |
| 7,258,686 B2 | 8/2007 | Maeda et al. | |
| 7,275,829 B2 | 10/2007 | Sugiura | |
| 2003/0223037 A1* | 12/2003 | Chernyak | 351/209 |
| 2004/0243113 A1 | 12/2004 | Sugiura et al. | |

FOREIGN PATENT DOCUMENTS

| | | |
|---|---|---|
| JP | A-04-242626 | 8/1992 |
| JP | A-6-18774 | 1/1994 |
| JP | A-9-149914 | 6/1997 |
| JP | A-10-503662 | 4/1998 |

(Continued)

OTHER PUBLICATIONS

Extended European Search Report issued in European Application No. 07832805.1 on Oct. 18, 2010.

(Continued)

*Primary Examiner* — Ryan Severson
*Assistant Examiner* — Anh Dang
(74) *Attorney, Agent, or Firm* — Oliff & Berridge, PLC

(57) ABSTRACT

A corneal surgery apparatus which comprises a laser irradiation optical system and an eye position change detection unit comprising an illumination optical system and an image pick-up camera picking up an anterior-segment image of a patient's eye and detecting the change in eye position based on an iris pattern in the image, and is arranged such that an irradiation position tracks movement of the eye to ablate a cornea, wherein the apparatus further comprises a contrast adjustment unit extracting a pupil portion and an iris portion based on luminance information of the image, and increasing/decreasing a set value of an illumination light amount and/or a set value of a gain of the camera to increase a contrast of the pupil portion to the iris portion and/or a contrast of the iris pattern within a range that luminance at the iris portion is not saturated.

4 Claims, 3 Drawing Sheets

(56) References Cited

FOREIGN PATENT DOCUMENTS

| | | |
|---|---|---|
| JP | A-10-192333 | 7/1998 |
| JP | A-11-226048 | 8/1999 |
| JP | A-2001-269317 | 10/2001 |
| JP | A-2003-506139 | 2/2003 |
| JP | A-2003-511206 | 3/2003 |
| JP | A-2004-89215 | 3/2004 |
| JP | A-2004-215889 | 8/2004 |
| JP | A-2004-261515 | 9/2004 |
| JP | A-2004-290535 | 10/2004 |
| JP | A-2004-351152 | 12/2004 |
| WO | WO 94/07447 | 4/1994 |
| WO | WO 95/28989 | 11/1995 |
| WO | WO 01/10338 A2 | 2/2001 |
| WO | WO 01/28476 A1 | 4/2001 |

OTHER PUBLICATIONS

Japanese Patent Office, Notification of Reason(s) for Refusal mailed Mar. 13, 2012 in Japanese Patent Application No. 2006-322648 w/English-language Translation.

Feb. 26, 2013 European Search Report issued in European Patent Application No. 07 832 805.1.

* cited by examiner

CORNEAL SURGERY APPARATUS

TECHNICAL FIELD

The present invention relates to a corneal surgery apparatus for ablating a cornea with a laser beam.

BACKGROUND ART

As a corneal surgery apparatus for ablating a cornea with a pulsed ultraviolet (UV) laser beam such as an excimer laser, there is known an apparatus which have a configuration such that an irradiation position of a laser beam is changed two-dimensionally on a cornea using a galvano mirror or other components (See Japanese Patent Application Unexamined Publication No. Hei11-226048). An apparatus of this kind has an eye tracking function which is arranged to track movement of an eye during a surgical operation, and irradiate an intended position with a laser beam. As the eye tracking function, there is known an eye tracking function which is arranged to pick up an anterior-segment image of a patient's eye with an image-pickup camera, and detects change in eye position including eye torsion by detecting a pupil edge that is a boundary of a pupil and an iris in the anterior-segment image, and an iris pattern (See published Japanese translation of PCT international publication for patent application No. 2003-511206).

DISCLOSURE OF THE INVENTION

Problem to be Solved by the Invention

However, reflection characteristics of anterior segments of patients' eyes differ due to patients' eyes or surgical conditions. For example, the amount of reflected light from an iris portion varies depending on the amount of pigments in the iris, which varies among races because many Westerners have blue eyes and many Asian have brown eyes, so that contrasts of the anterior-segment images picked up with an image-pickup camera differ from each other. In addition, in a surgery method called "LASIK" (Laser Assisted in Situ Keratomileusis) in which a corneal flap is formed to remove a corneal stoma from an eye, the amount of reflected light from an iris portion of the eye differs from that of an eye on which a corneal flap is not formed. For this reason, even when setting the amount of an illumination light for picking up an image of an eye with an image pick-up camera and the sensitivity of the image pick-up camera with reference to an average eye, difficulties arise in detecting an iris pattern based on which eye torsion is detected, due to differences among the reflected light amounts of patients' eyes.

In addition, even if a pupil and the iris pattern of the patient's eye can be detected at the initiation of a surgical operation, a pupil size of the patient's eye could significantly change during the surgical operation due to tension felt by the patient. When the pupil size significantly changes during the surgical operation, the iris pattern also changes from an iris pattern in an image obtained as a standard for alignment of an eye at the initiation of the surgical operation, so that a matching process of the iris patterns cannot be performed, resulting in degradation in detection accuracy and a detection error.

The present invention has been made in view of the above problems in the prior arts and has an object to provide a corneal surgery apparatus capable of improving success rates of detecting a pupil and an iris pattern of a patient's eye and tracking movement of the patient's eye to appropriately perform laser irradiation.

Means for Solving the Problems

To solve the above problems, a corneal surgery apparatus according to the present invention is characterized as having configurations described below.

(1) A corneal surgery apparatus which comprises a laser irradiation optical system capable of changing an irradiation position with a laser beam emitted from a laser source on a cornea of a patient's eye, and an eye position change detection unit which comprises an illumination optical system arranged to illuminate an anterior segment of the patient's eye, and an image pick-up camera arranged to pickup an image of the anterior segment illuminated by the illumination optical system and is arranged to detect change in eye position including torsion of an eyeball of the patient's eye subjected to a surgical operation based on an iris pattern in the anterior-segment image picked up with the image pick-up camera, and is arranged such that the irradiation position with the laser beam which is applied by the laser irradiation optical system tracks movement of the patient's eye based on a result of the detection by the eye position change detection unit, and the cornea is ablated to a desired shape by the application of the laser beam, wherein the corneal surgery apparatus further comprises a contrast adjustment unit arranged to extract a pupil portion and an iris portion based on luminance information on the anterior-segment image picked up with the image pick-up camera and increase and decrease at least one of a set value of an illumination light amount of the illumination optical system and a set value of a gain of the image pick-up camera so as to increase at least one of a contrast of the pupil portion with respect to the iris portion and a contrast of the iris pattern within a range such that luminance at the iris portion is not saturated.

(2) The corneal surgery apparatus according to claim 1 wherein the contrast adjustment unit is arranged to extract the pupil portion and the iris portion based on the luminance information on the anterior-segment image picked up with the image pick-up camera each time at least one of the set value of the illumination light amount of the illumination optical system and the set value of the gain of the image pick-up camera is increasingly or decreasingly changed, and adjust the set value so that at least one of a difference between luminance at the extracted iris portion and luminance at the extracted pupil portion and a difference in luminance in the iris pattern is maximized or exceeds a predetermined reference value.

(3) A corneal surgery apparatus which comprises a laser irradiation optical system capable of changing an irradiation position with a laser beam emitted from a laser source on a cornea of a patient's eye, and an eye position change detection unit which comprises an illumination optical system arranged to illuminate an anterior segment of the patient's eye, and an image pick-up camera arranged to pick up an image of the anterior segment illuminated by the illumination optical system and is arranged to detect change in eye position including torsion of an eyeball of the patient's eye subjected to a surgical operation based on an iris pattern in the anterior-segment image picked up with the image pick-up camera, and is arranged such that the irradiation position with the laser beam which is applied by the laser irradiation optical system tracks movement of the patient's eye based on a result of the detection by the eye position change detection unit, and the cornea is ablated to a desired shape by the application of the laser beam, wherein the corneal surgery apparatus further comprises a projection optical system arranged to project a visible light beam onto the patient's eye, and a setting unit arranged to set an allowable range of, variation of a pupil size such that the iris pattern is detectable with respect to a pupil size at the time when the iris pattern used as a reference for the change in eye position is obtained by the eye position change detection unit, and further comprises a display control unit comprising a display unit arranged to display the anterior-segment image picked up with the image pick-up camera, and is arranged to display a guide mark indicating the allowable range of the variation of the pupil size which is set based on a pupil center of the anterior-segment image by the setting unit in a manner of being superimposed on the anterior-segment image displayed on the display unit, and a light-amount adjustment unit comprising an operation switch with which a light amount of the projection optical system is changed manually, or further comprises a light-amount adjustment unit arranged to determine whether or not the pupil size detected by the eye position detection unit goes beyond the allowable range of the variation of the pupil size set by the setting unit, and automatically adjust the light amount of the projection optical system based on a result of the determination.

Effect of the Invention

According to the present invention, it is possible to improve success rates of detecting a pupil and an iris pattern of a patient's eye and to track movement of the patient's eye to appropriately perform laser irradiation.

BRIEF DESCRIPTION OF THE DRAWINGS

FIG. 3 is a view illustrating an anterior segment image of a patient's eye displayed on a monitor 32a.

BEST MODE FOR CARRYING OUT THE INVENTION

Figure 1:
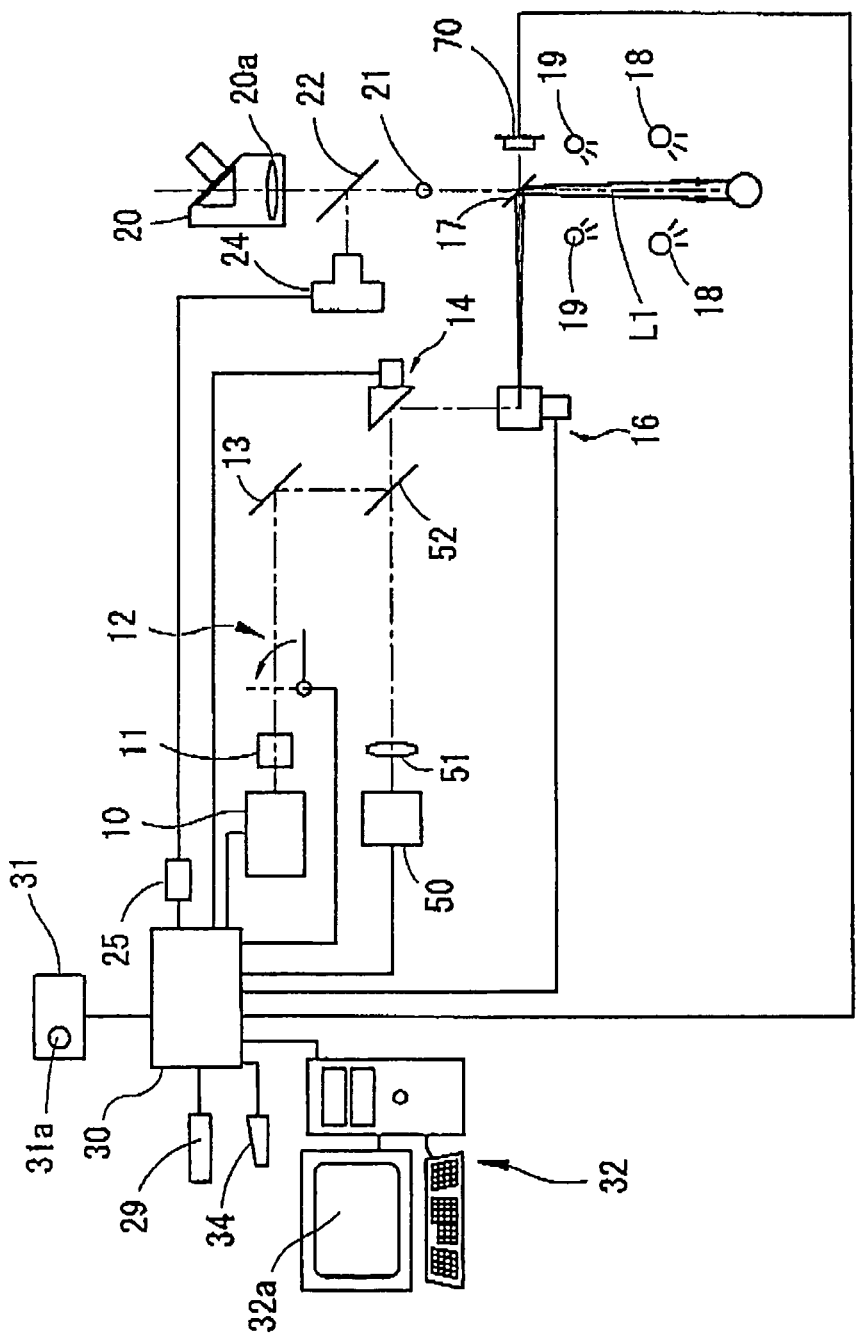
FIG. 1 is a view illustrating a schematic configuration of an optical system and a control system of a corneal surgery apparatus.

A detailed description of one preferred embodiment of the present invention is provided below with reference to the accompanying drawings. FIG. 1 is a view illustrating a schematic configuration of an optical system and a control system of a corneal irradiation apparatus according to the preferred embodiment of the present invention. A laser source 10 emits a pulsed ultraviolet (UV) laser beam for ablating a cornea. As the UV laser beam for ablating a cornea, an excimer laser with a wavelength of 193 nm is typically and preferably used. It is also preferable to use a laser beam which is emitted from a solid-state light source and a wavelength thereof is converted into a UV wavelength. A pulse frequency of the UV laser beam is set to be 40 Hz or more, and more preferably in the range of 200 to 500 Hz in order to shorten the time of a surgical operation.

A correcting optical system 11 is arranged to alter a beam shape of the laser beam emitted from the laser source 10 and form a laser beam of a circular spot. The size of a spot of the laser beam with which a cornea is to be irradiated is made about 0.5 to 1 mm by the correcting optical system 11. In addition, energy distribution in the laser beam spot is corrected by the correcting optical system 11 so as to become high in a center portion thereof and low in a peripheral portion thereof. The energy distribution is preferably the Gaussian distribution. The laser beam spot is applied so as to be superimposed on the cornea. Accordingly, smooth ablation is performed. A shutter 12 cuts off the laser beam emitted from the laser source 10, and is removed from an optical path in response to a trigger signal for laser irradiation. The shutter 12 cuts off the optical path when an abnormal condition is found. A reflection mirror 13 reflects the UV laser beam.

A visible laser source 50 that is a light source of a semiconductor laser or other lasers emits a visible laser beam with a wavelength of 630 nm which is to be an aiming beam. The visible laser beam emitted from the visible laser source 50 is made into a substantially parallel light by a lens 51. A dichroic mirror 52 has a property of totally reflecting the UV laser beam and transmitting the visible laser beam from the visible laser source 50. The UV laser beam from the laser source 10 and the visible laser beam from the visible laser source 50 are synthesized so as to be coaxial with each other by the dichroic mirror 52.

The UV laser beam and the visible laser beam coaxially synthesized by the dichroic mirror 52 is two-dimensionally scanned on the cornea at high speed by a scanning optical system (a laser-irradiation-position-changing optical system) consisting of galvano mirrors 14 and 16. The galvano mirrors 14 and 16 are each provided with a scanning mirror and a driving unit arranged to rotate the scanning mirror, a detailed illustration of which is omitted. The UV laser beam and the visible laser beam reflected by the galvano mirror 16 head for a beam splitter 17. The beam splitter 17 has a property of reflecting most of the UV laser beam and the visible laser beam and guiding them to a patient's eye E and transmitting the rest of the laser beams. The laser beams transmitted through the beam splitter 17 enter an energy monitor 70. The energy monitor 70 monitors an energy amount of the UV laser beam and sends the result to a control unit 30. The beam splitter 17 further has a property of transmitting infrared light. The UV laser beam and the visible laser beam reflected by the beam splitter 17 are coaxially directed to the cornea of the patient in a recumbent position on a bed (unillustrated) An infrared illumination light source (an infrared illumination unit) 18 illuminates an anterior segment of the patient's eye. The illumination light source 18 is connected to the control unit 30 by which an illumination light amount of the illumination light source 18 is controlled.

A binocular microscope 20 is provided on an opposite side of the patient's eye E with respect to the beam splitter 17. A surgeon observes the patient's eye E illuminated by a visible-light illumination unit 19 under the microscope 20. The visible-light illumination unit 19 arranged to project a visible light beam to the patient's eye is connected to the control unit 30 and has a configuration such that an illumination light amount thereof is changed through an operation by the surgeon or is changed by the control unit 30. A fixation light 21 is disposed on an optical axis L1 of an objective lens 20a of the microscope 20, and the patient's eye is fixated on the fixation light 21 during a surgical operation. The optical axis L1 of the objective lens 20a of the microscope 20 and central axes of the UV laser beam and the visible laser beam (the aiming beam) reflected by the galvano mirrors 14 and 16 are synthesized so as to be substantially coaxial by the beam splitter 17.

A beam splitter 22 having a property of reflecting the infrared light and transmitting the visible beam is disposed between the microscope 20 and the beam splitter 17, and an image pick-up camera (a photographing unit) 24 for picking up an image of the patient's eye is disposed on a reflecting side of the beam splitter 22. The image pick-up camera 24 is provided with an image pick-up element for photo-receiving the infrared light, and an output of the image pick-up camera 24 is sent to an image processing unit 25 to which the image pick-up camera 24 is connected.

An eye position change detection unit arranged to detect change in eye position including torsion of an eyeball of the patient's eye includes the illumination light source 18, the image pick-up camera 24 and the image processing unit 25. The image processing unit 25 is arranged to detect a pupil position of the patient's eye by processing the image (an image signal) picked up with the image pick-up camera 24. The pupil position can be obtained in various manners such that a pupil edge that is a boundary of a pupil and an iris is extracted and the barycenter of the pupil edge is set as a pupil center, and that a geometric center of the pupil edge in x- and y-directions of the image pick-up camera 24 is set as the pupil center. The detection result of the pupil position is used when the irradiation position with the laser beam is made to track the movement of the patient's eye. Further, the image processing unit 25 processes the image by the image pick-up camera 24 and extracts an iris pattern of the patient's eye. Based on the iris pattern, the torsion of the eyeball with respect to the substantial pupil center of the patient's eye is detected. Techniques to extract characteristic points of an iris disclosed in published Japanese translation of PCT international publication for patent application No. 2003-511206 and Japanese Patent Application Unexamined Publication No. 2004-89215 can be applied to the present invention.

In addition, the image processing unit 25 determines whether or not a contrast of a pupil portion and a contrast of the iris pattern are appropriate. Based on the determination result by the image processing unit 25, the control unit 30 adjusts a set value of the light amount of the illumination light source 18 so as to increase a contrast of an iris portion with respect to the pupil portion and the contrast of the iris pattern. By this operation, accuracy in detecting the pupil edge and the iris pattern is enhanced, and change in position of the patient's eye is detected. The detection of change in position of the patient's eye is achieved by making the extraction of characteristics of the iris and performing an arithmetic operation with the combined use of the image processing unit 25 and the control unit 30.

The laser source 10, the visible laser source 50, the galvano mirrors 14 and 16, the image processing unit 25, the shutter 12, the energy monitor 70 and other components are connected to the control unit 30. A computer unit 32 has a function of making an arithmetic operation of shot data (ablation data). The computer unit 32 is provided with a key board, a mouse and other components each acting as an input unit, and a monitor 32a acting as a display unit. The monitor 32a has a function of displaying an anterior-segment image to be described later. Upon input of data on characteristics of the patient's eye from an external measuring device (a device to obtain refractive power distribution, aberration distribution, a corneal topography or other data on the patient's eye) (unillustrated) using memory media or a communication cable (both unillustrated), the computer unit 32 obtains an ablation profile of the cornea based on the data on the characteristics of the patient's eye, and thereafter, finds the shot data based on the ablation profile. At this time, the anterior-segment image of the patient's eye is obtained along with the data on the characteristics of the patient's eye.

The shot data (ablation data) found by the computer unit 32 includes data on relationships between an irradiation position and a shot number of the laser beam spot. The shot data found by the computer unit 32 is inputted into the control unit 30, and the control unit 30 controls the galvano mirrors 14 and 16 and other components based on the shot data. A footswitch 34 is arranged to input a trigger signal for emitting the UV laser beam from the laser source 10. A memory 29 is a storage unit arranged to store the shot data, the anterior-segment image, a result of the arithmetic operation by the control unit 30, and other data. A controller 31 has switches for inputting various command signals into the apparatus.

Figure 2A:
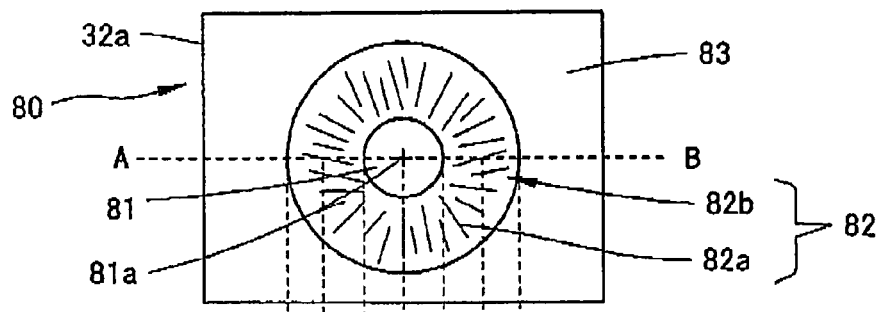
FIGS. 2A to 2D are views for explaining a contrast adjustment manner by which accuracy in detecting a pupil edge and an iris pattern from an anterior-segment image of a patient's eye is improved.

Next, a description of a manner of adjusting a contrast in order to improve accuracy in detecting the pupil edge and the iris pattern from the anterior-segment image of the patient's eye picked up with the image pick-up camera 24 is described. FIG. 2A is a view schematically illustrating the anterior-segment image of the patient' eye picked up with the image pick-up camera 24. In an anterior-segment image 80 shown in FIG. 2A, there are illustrated a pupil 81, an iris 82 and a sclera 83. A pupil center position 81a is found from the pupil edge which is the boundary of the pupil 81 and the iris 82. An iris pattern 82a is formed by wrinkles and muscles. Iris tissue 82b containing melanin pigments is schematically illustrated. As described above, because the amount of pigments such as melanin pigments varies among races or with other factors, reflectance of the iris tissue 82b and the iris pattern 82a with respect to illumination light varies. In FIG. 2A, the pupil 81 is displayed dark, the sclera 83 is displayed bright, and the iris 82 is displayed reasonably bright (the pattern 82a is displayed dark and the tissue 82b is displayed reasonably bright).

Figure 2B:
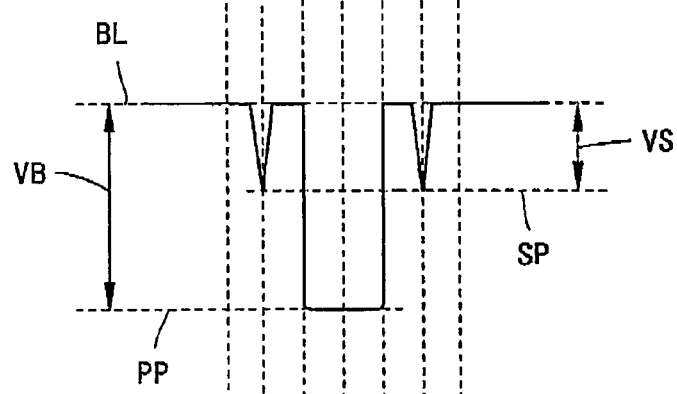
Figure 2C:
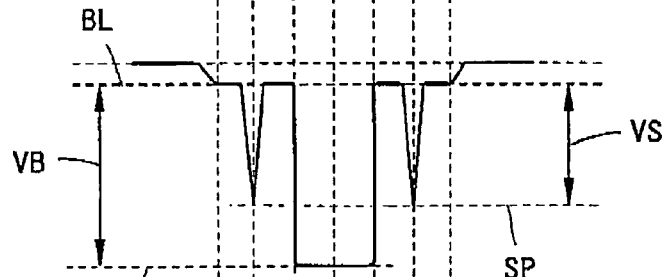
Figure 2D:
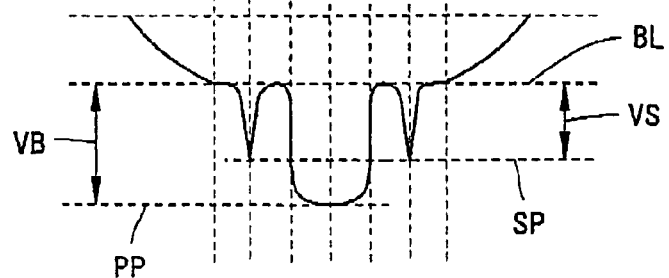

FIGS. 2B, 2C and 2D are views illustrating luminance distribution on the dotted line A-B in the anterior-segment image 80 shown in FIG. 2A. FIGS. 2B, 2C and 2D illustrate illumination distribution in a case where the amount of reflected light from the anterior segment is gradually decreased by arranging FIGS. 2B, 2C and 2D in this order in a direction such that the amount of infrared illumination light is gradually decreased. In each of FIGS. 2B, 2C and 2D, a position on the line A-B is indicated by a horizontal axis and luminance in the anterior-segment image picked up with the image pick-up camera 24 is indicated by a vertical axis. Dotted lines are drawn from FIG. 2A, and each luminance at portions in the anterior-segment image, the portions corresponding to the dotted lines, is plotted. The line A-B defines a line (pixels aligned in a horizontal line) on the anterior-segment image which passes through the pupil center found by the image processing.

In FIGS. 2B, 2C and 2D, a portion exhibiting the lowest luminance kept over the longest distance is extracted as a pupil portion at luminance PP. Viewing a rightward region and a leftward region of the pupil portion at the luminance PP, portions at luminance SP which exhibit low luminance after having exhibited high luminance are extracted as the iris pattern 82a of the iris 82. Further, in a case where a plurality of portions are found exhibiting low luminance after having exhibited high luminance, these portions are also extracted as the iris pattern 82a. Portions at luminance BL exhibiting high luminance on both sides of the iris pattern 82a are extracted as the iris tissue 82b that is a background of the iris pattern 82a. It is added that a portion exhibiting luminance higher than that of the iris tissue 82b, if any, is extracted as the sclera.

In this preferred embodiment of the present invention, the difference between the luminance SP extracted as the iris pattern 82a and the luminance BL extracted as the iris tissue 82b is referred to as a luminance difference VS. The difference between the luminance PP at the pupil portion and the luminance BL at the iris tissue 82b is referred to as a luminance difference VB. Determination as to whether or not the contrast is appropriate is made based on the luminance difference VS within a range such that the portions at the luminance BL are not saturated (with no halation). The illumination light amount of the illumination light source 18 is decreasingly changed from an initial value continuously or step-by-step, and variation in the luminance difference VS is checked each time the illumination light amount is changed. Additionally, the illumination light amount of the illumination light source 18 is increasingly changed from the initial value continuously or step-by-step, and variation in the luminance difference VS is checked each time the illumination light amount is changed. At this time, when the luminance difference VS is maximized, the contrast increases accordingly. In FIGS. 2B, 2C and 2D, FIG. 2D illustrates the luminance distribution in a case where the illumination light amount is decreasingly changed with respect to that in FIG. 2C. As a result, the luminance difference VS in FIG. 2C is larger than that in FIG. 2D, and the contrast in FIG. 2C increases compared with that in FIG. 2D accordingly. On the other hand, FIG. 2B illustrates the luminance distribution in a case where the illumination light amount is increasingly changed with respect to that in FIG. 2C. As a result, the luminance difference VS in FIG. 2C is larger than that in FIG. 2B, and the contrast in FIG. 2C increases compared with that in FIG. 2B accordingly. In FIG. 2B, the portions at the luminance BL are saturated, meaning that the illumination light amount is too large.

As described above, the control unit 30 adjusts the set value of the illumination light amount of the illumination light source 18 so as to maximize the luminance difference VS which is extracted from the anterior-segment image picked up with the image pick-up camera 24, each time the illumination light amount of the illumination light source 18 is increasingly or decreasingly changed. By this operation, the contrast of the iris pattern 82a (a contrast between the iris tissue 82b and the iris pattern 82a) is increased, whereby accuracy in detecting the iris pattern is improved. However, it is essential only that the luminance difference VS exceed a predetermined reference value such that the iris pattern can be detected, and it is not necessary that the luminance difference VS is maximized. Hence, the set value of the illumination light amount of the illumination light source 18 may be set at this stage.

It is preferable that the contrast of the iris pattern 82a is directly observed based on the luminance difference VS in order to detect the iris pattern; however, the luminance difference VB between the luminance PP at the pupil portion 81 and the luminance BL at the iris tissue 82b may be used alternatively to the luminance difference VS. It is because there is a correlation between variation in the luminance difference VB and variation in the contrast of the iris pattern. When the luminance difference VB is maximized, the contrast between the portion at the luminance BL of the iris 82 (the iris tissue 82b) and the portion at the luminance PP of the pupil 81 is increased, whereby accuracy in detecting the pupil edge which is the boundary of the iris 82 and the pupil 81 is improved. However, it is essential only that the luminance difference VB exceed a predetermined reference value such that the iris pattern can be detected, and it is not necessary that the luminance difference VB is maximized. Further, the luminance differences VS and VB may be simultaneously used. For example, when the luminance difference VS is nearly maximized, the control unit 30 controls the illumination light source 18 to increasingly or decreasingly change the amount of the infrared illumination light so as to maximize the luminance difference VB additionally and detects movement of the eye.

The automated contrast adjustment thus described is performed based on a signal inputted upon press of a switch 31a for contrast adjustment provided to the controller 31 prior to the initiation of automated tracking of the eye performed by the image processing unit 25. Alternatively, the automated contrast adjustment is performed in response to a trigger signal automatically emitted from the control unit 30 when a detection error of the iris pattern is found and a message to that effect is displayed on the monitor 32a. A detection error of the iris pattern can be determined on the basis of whether or not the luminance difference VS or the luminance difference VB exceeds the predetermined reference value.

Upon input of the starting signal of automated contrast adjustment, the image processing unit 25 successively obtains the anterior-segment image from the image pick-up camera 24 each time the control unit 30 controls the illumination light source 18 to increasingly or decreasingly change the amount of the infrared illumination light, and performs a determination process as to whether or not the luminance difference is maximized or exceeds the predetermined reference value. The control unit 30 obtains the amount of the infrared illumination light of the illumination light source 18 through the determination process, controls the memory 29 to store the amount, and sets the amount of the infrared illumination light of the illumination light source 18 for the patient's eye subjected to the surgical operation.

The luminance distribution in the anterior-segment image illustrated in FIGS. 2B, 2C and 2D are extracted on the line A-B which passes through the pupil center 81a; however, the present invention is not limited thereto. The luminance distribution may be extracted on a line which is deviated a little from the pupil center 81a (i.e., translated) as long as including information on the pupil and the iris used as a reference for luminance distribution.

The luminance distribution may be extracted not on a single line. That is, the luminance distribution may be extracted on lines translated from the line passing through the pupil center. For example, the line passing through the pupil center and another line deviated from the mentioned line by 1 mm are used for extracting the luminance distribution, and contrasts are determined based on the luminance distribution using the above-described manners. It is also preferable that these lines do not have a positional relation of being parallel to each other but have a positional relation such that the luminance distribution is extracted on radial lines passing through the vicinity of the pupil center.

Next, a description of operation of the apparatus during the surgical operation including the automated contrast adjustment will be provided. The surgeon performs alignment of the apparatus so as to have a predetermined positional relation such that the laser irradiation of the eye of the patient who is in a recumbent position can be performed, while observing the patient's eye under the microscope 20. After the alignment, the contrast-adjustment switch 31a is pressed (alternatively, the trigger signal is automatically emitted when a detection error is found), and the image processing unit 25 and the control unit 30 perform the automated contrast adjustment as described above. This operation allows the image processing unit 25 to detect change in position of the patient's eye, whereby the automated tracking is ready to be performed. The monitor 32a displays a message to that effect.

After the alignment of the apparatus for the laser irradiation of the patient's eye is completed, when an automatedtracking-initiation switch mounted on the controller 31 is pressed, a pupil position (the pupil center in this description) and the iris pattern are detected from the anterior-segment image picked up with the image pick-up camera 24, the process is performed, and a reference state of the patient's eye for the automated tracking is stored in the memory 29. When the surgeon steps on a foot pedal, the laser irradiation is initiated. During the laser irradiation, it is possible to observe the aiming beam from the visible laser source 50 irradiating the cornea. The control unit 30 controls the galvano mirrors 14 and 16 to move using control data based on the shot data. The laser beam spot is two-dimensionally scanned on the cornea by the galvano mirrors 14 and 16, and the cornea is ablated to a desired shape. Meanwhile, the control unit 30 monitors the movement of the patient' eye with respect to the reference state at the initiation of the surgical operation, based on the pupil position and the iris pattern detected by the image pick-up camera 24 and the image processing unit 25. Detecting that the patient's eye is moved, the control unit 30 controls the galvano mirrors 14 and 16 to move such that the laser beam spot tracks the patient's eye by the amount of the deviation from the reference state. When the patient's eye significantly moves beyond an allowable range, the laser irradiation is stopped by closing the shutter 12, and is restarted when the patient's eye moves within a trackable range. In addition, there is also performed eye-torsion tracking operation of the patient's eye based on the iris pattern. That is, the image processing unit 25 and the control unit 30 perform an arithmetic operation to find how much the patient's eye rotates during the surgical operation from a difference in the iris pattern (a difference in the iris pattern rotated about the pupil center) by comparing the anterior-segment images obtained by the image pick-up camera 24 at given intervals, e.g., every one frame, and then, the control unit 30 controls the galvano mirrors 14 and 16 to move such that the laser beam spot tracks the patient's eye by the amount of the torsion(rotation), similarly to the above-described example. At this time, an angle corresponding to the torsion having been obtained prior to the laser irradiation and is stored in the memory 29 is added as an offset value to the arithmetic operation. When the patient's eye significantly rotated beyond an allowable range, the laser irradiation is stopped by closing the shutter 12 and the surgeon is informed of the stop of the laser irradiation (unillustrated).

The arithmetic operation to find a change of the torsion is thus performed by comparing the anterior-segment images obtained before and after the torsion change by the image pick-up camera 24, whereby the time for arithmetic processing can be reduced more than the time in the case of comparing anterior-segment images obtained by an external device. Accordingly, the torsion change can be detected in real time.

During the laser irradiation of the cornea while scanning the laser beam spot, the energy monitor 70 obtains an amount of energy (mJ) every shot of the laser beam and sends them to the control unit 30. The control unit 30 makes a comparison between the thus-obtained amount of energy and a set amount, and when a difference therebetween falls out of an allowable range, the control unit 30 stops the laser irradiation by closing the shutter 12, similarly to the above example, and prompts the surgeon's attention using the computer unit 32 or other components. By repeating this kind of operation, a predetermined corneal shape is obtained.

In the above description, the automated contrast adjustment is performed by increasing or decreasing the light amount of the illumination light source 18; however, the present invention is not limited thereto. It is also preferable that a gain of the sensitivity of the image pick-up camera 24 is adjusted by the image processing unit 25 or the control unit 30. That is to say, each time the gain of the image pick-up camera 24 is increased or decreased, values of the contrasts of the pupil and the iris pattern in the anterior-segment image picked up with the image pick-up camera 24 are set by adjusting the gain of the image pick-up camera 24 so that the luminance difference VS is maximized or exceeds a predetermined reference value within a range such that the portions at luminance BL are not saturated (with no halation) as in FIGS. 2B, 2C and 2D, instead of changing the illumination light amount. Also in this case, the luminance difference VB may be used alternatively to the luminance difference VS, or may be used in combination with the luminance difference VS. Further, the gain adjustment of the image pick-up camera 24 and the light-amount adjustment of the illumination light source 18 may be used in combination.

The above-described automated contrast adjustment is performed prior to the laser irradiation of the patient's eye; however, it is also preferable to arrange the automated contrast adjustment to be additionally performed during the ablation with the laser irradiation (during the surgical operation) by periodically detecting whether or not the contrast in the anterior-segment image is appropriate. This arrangement allows the apparatus to respond to the variation in the contrast of the anterior-segment image which is made with the ablation of corneal tissue of the patient's eye, whereby change in position of the patient's eye can be steadily detected by the apparatus. Therefore, a surgical operation responsive to cyclotorsion of the patient's eye in real time is made possible, improving accuracy of a laser surgical operation such as astigmatic correction. It is also preferable that the above-mentioned automated contrast adjustment is performed based on a signal to inform that the movement or the torsion of the patient's eye cannot be detected by the eye position change detection unit.

In the above-described embodiment of the present invention, adjustment of the infrared illumination light amount for increasing the contrasts of the pupil edge and the iris pattern is performed after the alignment; however, the present invention is not limited thereto. It is also preferable that the eye position change detection unit arranged to detect the change in position of the patient's eye in the x- and y-directions is driven after the alignment, and the contrast adjustment is performed while the eye position change detection unit is driven. In the above description, the contrast of the pupil edge is improved along with the contrast of the iris pattern; however, in many cases, the contrast of the pupil edge (the luminance difference between the pupil portion and the iris portion) is higher than the luminance difference of the iris pattern and is accordingly enough for performing image processing such as pupil-diameter extraction, even if the contrast of the iris pattern is low. Therefore, the above-described contrast adjustment of the iris pattern can be performed while the eye position change detection unit is driven to detect the change in position of the patient's eye in the x- and Y-directions. Hence, the image processing unit 25 can keep detecting the pupil center, allowing extraction of the luminance distribution at the same portion in extraction of the luminance distribution with respect to the pupil center. It is preferable that the contrasts of the iris pattern (e.g., the luminance differences VS) in the luminance distribution obtained for every infrared illumination light amount are evaluated as to variation among luminance values obtained at the portion (the same iris pattern), so that when the contrast adjustment is performed while the eye position change detection unit is driven to detect the change in position of the patient's eye in the x-and Y-directions, accuracy in contrast adjustment is improved and the time of a surgical operation is shortened.

It is added that the pupil center is used as an example of identifying the pupil position, and other manners may be used only if the pupil position can be identified. For example, a distinctive feature in the pupil edge, if any, may be used for identifying the pupil position.

Described-above is an example of the automated contrast adjustment of an anterior-segment image which changes due to reflection characteristics of a patient's eye, which is preferable to perform when a pupil size of a patient's eye significantly changes during a surgical operation. A manner for this adjustment will be described.

Figure 3:
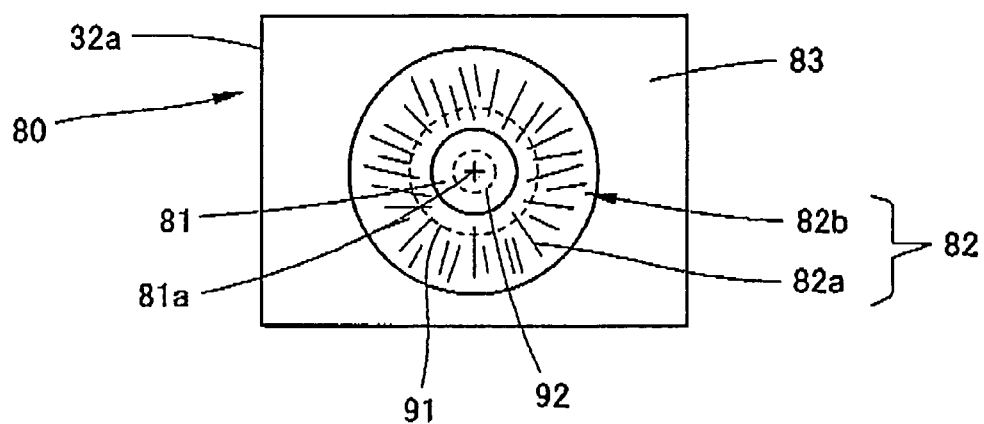

FIG. 3 is a view illustrating the anterior segment image of the patient's eye displayed on the monitor 32a. On the monitor 32a, a circular guide mark 91 for a maximum pupil diameter and a circular guide mark 92 for a minimum pupil diameter are displayed as guide marks indicating allowable ranges of the pupil size which varies during the surgical operation. In FIG. 3, the guide marks 91 and 92 are illustrated with dotted lines. The guide marks 91 and 92 are generated by the computer unit 32 based on the pupil center 81a of the pupil 81 detected by the image processing of the image processing unit 25, and are displayed in a manner of being superimposed on the anterior-segment image picked up with the image pick-up camera 24. When the pupil center of the anterior-segment image moves, the guide marks 91 and 92 are displayed in accordance with the moved pupil center.

The allowable ranges of the guide marks 91 and 92 are set by the control unit 30 in the following manner. Upon press of the automated-tracking-initiation switch and the automated tracking is initiated, the control unit 30 obtains the size of the pupil 81 of the anterior-segment image which is picked up with the image pick-up camera 24 and obtained by the image processing unit 25. Using the pupil size as a reference, the allowable ranges to be indicated by the guide marks 91 and 92 are set based on an allowable range such that a pattern matching process can be performed (data of the allowable range has been previously stored in the memory 29) when the image processing unit 25 extracts and processes the iris pattern. For example, the allowable range for the image processing unit 25 to perform the pattern matching process of the iris pattern with respect to the variation of the pupil size is set to be ±50% based on a pupil diameter D of the patient's eye which is obtained when the automated tracking is initiated (used as the pupil diameter D is an averaged diameter).

The guide mark 91 for the maximum pupil diameter is a circle which is made larger than the pupil diameter D by 50%, and indicates the upper limit of expansion (mydriasis) of the pupil 81. Meanwhile, the guide mark 92 for the minimum pupil diameter is a circle which is smaller than the pupil diameter D by 50%, and indicates the lower limit of contraction (miosis) of the pupil 81. When the size of the pupil subjected to the surgical operation becomes larger than the upper limit indicated by the guide mark 91, or smaller than the lower limit indicated by the guide mark 92, the pupil diameter, the pupil center and the iris pattern, which are used for detecting the change in position of the patient's eye, are determined such that they are significantly changed, whereby the accuracy of the pattern matching of the iris pattern is degraded and the detection error of the automated tracking is apt to be caused. In addition, the position of the pupil center shifts in accordance with the significant variation of the pupil size, whereby the accuracy in detecting the torsion change with respect to the pupil center is degraded.

As described above, displaying the upper and lower limits of the variation of the pupil diameter in the manner of being superimposed on the anterior-segment image allows the surgeon to easily recognize a detection status of the change in position of the patient's eye during the surgical operation, and further allow the surgeon to easily adjust the amount of the visible illumination light so as to ensure continuous operation of the eye position change detection (an automated tracking function) of the patient's eye.

When the pupil 81 observed on the monitor 32a is changed in size during the surgical operation, and is about to go beyond the size of the guide mark 91 for the maximum pupil diameter, the surgeon (or an assistant) manipulates a light-amount adjustment switch mounted on the controller 31 to increase the illumination light amount of the visible-light illumination unit 19, whereby the pupil of the patient's eye is contracted. On the other hand, when the pupil 81 is changed in size, and is about to go within the size of the guide mark 92 for the minimum pupil diameter, the surgeon (or the assistant) decreases the illumination light amount of the visible-light illumination unit 19, whereby the pupil of the patient's eye is expanded and made to stay within the range between the guide marks 91 and 92. The above-described adjustment of the pupil size of the patient's eye allows easily maintaining the eye position change detection of the patient's eye during the surgical operation. Further, the easily maintaining the eye position change detection of the patient's eye improves accuracy of the surgical operation, and shortens the time of a surgical operation.

In the above-described preferred embodiment of the present invention, the circles indicating the upper and lower limits of the variation of the pupil diameter are displayed as the guide marks 91 and 92 in the manner of being superimposed on the monitor 32a; however, the manner of the display is not limited thereto. It is also preferable to display only the guide mark 91 for the maximum pupil diameter. This is because, in many cases, the pupil gradually opens during the laser irradiation, and therefore, only the guide mark 91 may be displayed.

In addition, the light amount of the visible-light illumination unit 19 may be adjusted not by the surgeon's manual operation but in an automated manner. For example, the pupil diameter is extracted as a substantial circle by the image processing of the image processing unit 25, and when the substantial circle is about to go beyond the size equivalent to the guide mark 91 for the maximum pupil diameter, a signal to that effect is sent to the control unit 30. Based on the signal, the control unit 30 controls the visible-light illumination unit 19 to increase the light amount in order for the pupil diameter of the patient's eye not to go beyond the size of the guide mark 91 for the maximum pupil diameter. On the other hand, when the substantial circle is about to go within the size equivalent to the guide mark 92 for the minimum pupil diameter, the control unit 30 controls the visible-light illumination unit 19 to decrease the light amount in order for the pupil diameter of the patient's eye to stay within the allowable range. This operation allows the eye position change detection of the patient's eye to be automatically maintained by the eye position change detection unit.

It is added that the guide marks 91 and 92 indicating the upper and lower limits of the variation of the pupil diameter described in the preferred embodiment of the present invention do not have to strictly define the upper and lower limits, and it is essential only to have estimated sizes of the upper and lower limits.

The present modified preferred embodiment of the present invention may be practiced in combination with the above-described preferred embodiment of the present invention. In this case, the contrast by the infrared illumination can be maintained high, and the pupil diameter of the patient's eye can be easily maintained constant in the eye position change detection of the patient's eye. This makes it possible to shorten the time of a surgical operation and improve accuracy of the surgical operation.

In the above-described preferred embodiments of the present invention, the pupil diameter of the patient's eye is adjusted by adjusting the light amount of the visible-light illumination unit 19 arranged to illuminate the patient's eye; however, the present invention is not limited thereto. It is also preferable that the pupil diameter of the patient's eye is adjusted by adjusting the light amount of a fixation lamp (visible light) which facilitates fixation of the patient's eye.

In the above-described embodiments of the present invention, the monitor 32a of the computer unit 32 displays the patient's eye on which guide marks are displayed in the superimposing manner; however, the present invention is not limited thereto. It is also preferable to provide a monitor separately from the computer unit 32. For example, an infrared monitor for displaying the patient's eye may be provided in the vicinity of the microscope 20. This configuration allows easily checking the patient's eye displayed on the monitor. In addition, it is also preferable that a beam splitter and a superimposed-display unit are disposed on an observation optical path of the microscope 20 to form a head-up display, and the guide marks 91 and 92 which are displayed on the monitor 32 in the above-described preferred embodiments of the present invention are displayed so as to be superimposed on an observed image which is observed under the microscope 20. This allows the surgeon to check the guide marks or other marks without looking aside from the microscope 20.

The invention claimed is:

1. A corneal surgery apparatus, which comprises:
a laser irradiation optical system capable of changing an irradiation position with a laser beam emitted from a laser source on a cornea of a patient's eye; and
an eye position change detection unit, which comprises:
an illumination optical system arranged to illuminate an anterior-segment of the patient's eye with infrared illumination light; and
an image pick-up camera arranged to pick up an image of the anterior-segment illuminated by the illumination optical system, and is arranged to detect change in eye position including torsion of an eyeball of the patient's eye subjected to a surgical operation based on an iris pattern in the anterior-segment image picked up with the image pick-up camera, and is arranged such that the irradiation position with the laser beam which is applied by the laser irradiation optical system tracks movement of the patient's eye based on a result of the detection by the eye position change detection unit, and the cornea is ablated to a desired shape by the application of the laser beam,
wherein the corneal surgery apparatus further comprises a control unit arranged to extract the iris pattern at an iris portion and a background of the iris pattern based on luminance information on the anterior-segment image picked up with the image pick-up camera, and adjust at least one of a set value of an illumination light amount of the illumination optical system and a set value of a gain of the image pick-up camera so that a luminance difference between the iris pattern and the background of the iris pattern is maximized or exceeds a predetermined reference value, and luminance at the iris pattern at the iris portion and the background of the iris pattern is not saturated.

2. The corneal surgery apparatus according to claim 1, further comprising:
a projection optical system arranged to project a visible light beam onto the patient's eye; and
a light-amount adjustment unit comprising an operation switch with which a light amount of the projection optical system is changed manually.

3. The corneal surgery apparatus according to claim 2, further comprising:
a setting unit arranged to set an allowable range of variation of a pupil size such that the iris pattern is detectable, the iris pattern being used as a reference for tracking the patient's eye; and
a display control unit comprising a display unit arranged to display the anterior-segment image picked up with the image pick-up camera, and is arranged to display a mark indicating the allowable range, which is set by the setting unit, in a manner of being superimposed on the anterior-segment image displayed on the display unit.

4. A corneal surgery apparatus, which comprises:
a laser irradiation optical system capable of changing an irradiation position with a laser beam emitted from a laser source on a cornea of a patient's eye; and
an eye position change detection unit, which includes:
an illumination optical system arranged to illuminate an anterior-segment of the patient's eye with infrared illumination light; and
an image pick-up camera arranged to pick up an image of the anterior-segment illuminated by the illumination optical system, and is arranged to detect change in eye position including torsion of an eyeball of the patient's eye subjected to a surgical operation based on an iris pattern in the anterior-segment image picked up with the image pick-up camera, and is arranged such that the irradiation position with the laser beam which is applied by the laser irradiation optical system tracks movement of the patient's eye based on a result of the detection by the eye position change detection unit, and the cornea is ablated to a desired shape by the application of the laser beam,
wherein the corneal surgery apparatus further comprises a control unit arranged to extract the iris pattern at an iris portion and a background of the iris pattern based on luminance information on the anterior-segment image picked up with the image pick-up camera, and adjust at least one of a set value of an illumination light amount of the illumination optical system and a set value of a gain of the image pick-up camera so that a luminance difference between the iris pattern and the background of the iris pattern is maximized or exceeds a predetermined reference value, and luminance at the iris pattern at the iris portion and the background of the iris pattern is not saturated;
a projection optical system arranged to project a visible light beam onto the patient's eye;
a setting unit arranged to set an allowable range of variation of a pupil size such that the iris pattern is detectable, the iris pattern being used as a reference for tracking the patient's eye; and
a light-amount adjustment unit arranged to determine whether or not the pupil size detected by the eye position detection unit goes beyond the allowable range during the surgical operation, and automatically adjust the light amount of the projection optical system based on a result of the determination.

* * * * *